(12) United States Patent
Raufman et al.

(10) Patent No.: US 6,733,483 B2
(45) Date of Patent: May 11, 2004

(54) ABSORBENT ARTICLE HAVING POSITIONING INDICIA

(75) Inventors: Michael Charles Raufman, Liberty Township, OH (US); Carmie S. Maloney, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 14 days.

(21) Appl. No.: 09/400,041

(22) Filed: Sep. 21, 1999

(65) Prior Publication Data

US 2002/0062117 A1 May 23, 2002

(51) Int. Cl.[7] .............................................. A61F 13/15
(52) U.S. Cl. .............................. 604/385.01; 604/385.03
(58) Field of Search ............................... D24/124–126; 604/385.01, 386, 387, 389, 390, 391

(56) References Cited

U.S. PATENT DOCUMENTS

| | | | |
|---|---|---|---|
| 3,638,651 A | 2/1972 | Torr ........................... 128/284 |
| 3,646,937 A | 3/1972 | Gellert ........................ 128/287 |
| 3,856,008 A | 12/1974 | Fowler et al. ............... 128/165 |
| 3,869,761 A | 3/1975 | Schaar .......................... 24/73 |
| 4,036,233 A | 7/1977 | Kozak ......................... 128/287 |
| 4,662,875 A | 5/1987 | Hirotsu et al. ............... 604/389 |
| 4,923,456 A | 5/1990 | Proxmire ..................... 604/391 |
| 4,936,840 A | 6/1990 | Proxmire ................... 604/385.2 |
| 5,019,070 A | 5/1991 | Ruben ......................... 604/387 |
| 5,133,707 A | 7/1992 | Rogers et al. ............... 604/389 |
| 5,275,588 A | 1/1994 | Matsumoto et al. ......... 604/372 |
| 5,324,279 A | 6/1994 | Lancaster et al. ............ 604/391 |
| 5,342,344 A | 8/1994 | Lancaster et al. ............ 604/387 |
| 5,531,731 A | 7/1996 | Brusky ........................ 604/390 |
| 5,897,546 A | 4/1999 | Kido et al. ................... 604/391 |
| 6,045,543 A | 4/2000 | Pozniak et al. ............ 604/385.1 |

FOREIGN PATENT DOCUMENTS

| | | | |
|---|---|---|---|
| EP | 0 756 855 A1 | 2/1997 | ............ A61F/13/58 |
| EP | 0 893 115 A2 | 1/1999 | ............ A61F/13/56 |
| GB | 2 135 568 | 9/1984 | ............ A41B/13/02 |
| GB | 2 267 024 A | 11/1993 | ............ A61F/13/66 |
| WO | WO 99/22688 | 5/1999 | ............ A61F/13/56 |
| WO | WO 00/35401 | 6/2000 | ............ A61F/13/56 |

OTHER PUBLICATIONS

International Search Report mailed Nov. 24, 2000 for PCT/IB00/01273.

*Primary Examiner*—Weilun Lo
*Assistant Examiner*—Michele Kidwell
(74) *Attorney, Agent, or Firm*—Jack L. Oney, Jr.; David M. Weirich; Ken K. Patel

(57) ABSTRACT

An absorbent article, such as a disposable diaper, adapted to be worn about the lower torso of a wearer. The diaper includes side panels and fastener elements for assembling the diaper about the body of the wearer. The outer surface of the diaper and the side panels or fastener tabs include indicia that complement each other and are provided to facilitate the proper and symmetrical application of the diaper to the wearer for maximum comfort and for optimal functioning of the diaper as a waste retention vehicle without leakage between the diaper and the legs of the wearer.

3 Claims, 9 Drawing Sheets

ABSORBENT ARTICLE HAVING POSITIONING INDICIA

FIELD OF THE INVENTION

The present invention relates to disposable absorbent articles, such as disposable diapers. More particularly, the present invention relates to a disposable absorbent article that includes side panels or fastener tabs that carry indicia cooperable with indicia carried on the outer face of the chassis or fastening surface to facilitate proper positioning of the article on the body of the wearer or for proper configuration of the diaper for disposal.

BACKGROUND OF THE INVENTION

Infants and other incontinent individuals wear absorbent articles such as diapers and incontinent briefs to receive and contain discharged urine and other body exudates. Such absorbent articles function both to contain the discharged materials and to isolate those materials from the body of the wearer and from the wearer's garments and bed clothing. Disposable absorbent articles having many different basic designs are known in the art. For example, U.S. Pat. No. 5,151,092 entitled "Absorbent Article With Dynamic Elastic Waist Feature Having a Predisposed Resilient Flexural Hinge," which issued on Sep. 29, 1992, to Buell et al., describes a basic disposable diaper structure that has achieved wide acceptance and considerable commercial success.

Disposable absorbent articles are often supplied in a form that requires assembly of the article relative to the body of the wearer. Such articles generally include fastener tabs for securing the article in position about the waist of the wearer. Examples of such known structures are disclosed in U.S. Pat. No. 5,037,416, entitled "Disposable Absorbent Article Having Elastically Extensible Topsheet," which issued on Aug. 6, 1991, to Allen et al.; U.S. Pat. No. 5,269,775, entitled "Trisection Topsheets for Disposable Absorbent Articles and Disposable Absorbent Articles Having Such Trisection Topsheets," which issued on Dec. 14, 1993, to Freeland et al.; and U.S. Pat. No. 5,624,422, entitled "Absorbent Article Having an Extendible Split Core," which issued on Apr. 29, 1997, to Allen.

Proper application and positioning of a disposable diaper that is in the conventional, substantially rectangular or hourglass form is important for the comfort of the wearer, and also for the proper functioning of the diaper. Unless one is especially careful in the course of applying a disposable diaper, it is very easy to apply the diaper to a wearer in a manner that results in the diaper not properly fitting to the wearer's body. For example, if the diaper is applied and fastened so that it is non-symmetrical, one of the leg openings that is formed by the longitudinal edges of the diaper when the diaper is applied and is worn is larger than the other leg opening. As a result, it is possible for unintended leakage to take place between the diaper leg opening and the wearer's leg on the side of the diaper having the larger leg opening. Additionally, the smaller leg opening might be too tight about the wearer's leg, causing discomfort. Thus, it is desirable to provide a means whereby the person applying a disposable diaper can do so simply and quickly, and in such a manner that the diaper is symmetrically and comfortably positioned on the wearer's body. It is also desirable to provide the diaperer with a simple way to determine how the used diaper should be configured for disposal.

The matter of facilitating the proper application and fastening of a disposable diaper has been addressed by others. For example, in U.S. Pat. No. 4,662,875, entitled "Absorbent Article," which issued on May 5, 1987, to Hirotsu et al., there is disclosed a positioning arrangement to aid in properly fitting a disposable diaper to a wearer. The disclosed positioning arrangement includes indicia that are provided on the outer face of the diaper backsheet, in the areas to which the tape fastener tabs are secured during application of the diaper. The indicia illustrated in that patent include a plurality of parallel, spaced, longitudinally-extending lines and a plurality of dots, each placed on and extending over a portion of the outer surface areas at which the fastener tabs are to be secured.

Another patent that discloses a tape fastener tab positioning arrangement is U.S. Pat. No. 5,897,546, entitled "Disposable Diaper Having a Fastening System," which issued on Apr. 27, 1999, to Kido et al. The improvement disclosed by Kido et al. resides in placing positioning indicia between the diaper backsheet and an overlying fastener tab-landing zone. The indicia are provided by longitudinally-extending strips of colored adhesive that serve to secure the landing zone strip in position on the backsheet. The color shows through the landing strip to provide placement guidance to one applying the diaper. Kido et al. point out that their approach does not require surface printing of the backsheet, and it also precludes contact by the wearer of the printed positioning indicia.

Despite the previously-disclosed attempts to provide fastener tab positioning indicia, it is desirable to further simplify the diaper application and fastening process. In that regard, it is desirable to enable diaper application and placement of the fastener tabs to be accomplished more accurately, more quickly, and more simply. Further, it is also desirable to provide a fastening system that can serve as a source of amusement to the applier and to the wearer, and that can serve to attract and temporarily hold the attention of the wearer during application, to thereby reduce the likelihood of wearer squirming or leg movement that can impede the diaper application process.

Accordingly, it would be desirable to provide an improved disposable absorbent article that includes an interactive fastening system, wherein the side panels or fastener tabs as well as the receiving zones to which the tabs or side panels are secured include indicia that facilitate positioning of the side panels or fastener tabs and that also can attract the attention of the wearer during the application process.

It would also be desirable to provide an absorbent article with an interactive fastening system that helps the user determine the proper wearing or disposal configuration by the use of predetermined complementary visual images produced when the side panels or fasteners are properly positioned on the outer cover of the chassis.

SUMMARY OF THE INVENTION

Briefly stated, in accordance with one aspect of the present invention, there is provided a disposable absorbent article that is worn about the waist and lower torso. The article includes a liquid impervious backsheet having an outer, garment-facing surface and an inner, body-facing surface. An absorbent core is provided adjacent the body-facing surface of the backsheet. The absorbent core has a shape to enable the core to be placed adjacent the crotch area of the body of a wearer and has the capacity to absorb liquids and to retain solids. A flexible, liquid-pervious topsheet overlies the absorbent core, The disposable absorbent article includes a longitudinal central axis and an outwardly-facing surface and an inwardly-facing surface. The chassis is adapted to extend from a back waist area of a wearer to a front waist area of the wearer, with the inwardly-facing surface overlying the wearer's stomach, crotch, and lower back. The chassis includes a first waist portion and a second waist portion. A pair of side panels and/or fastener tabs extend laterally outwardly from respective edge portions of the second waist portion of the article. The side panels each carry a fastening element for engagement with the outwardly-facing surface at the first waist portion of the article for securing the article in wearing position on the body of the wearer. The first waist portion of the article includes an outwardly-facing first indicium element carried on the outwardly-facing surface of the chassis, wherein the first indicium element is positioned symmetrically with the longitudinal central axis of the chassis. The side panels and/or fastener tabs each include a second indicium element. The first and second indicium elements are visually complementary with each other to define a predetermined visual image to facilitate application of the fastener elements to the outwardly-facing surface at the first waist portion of the chassis for proper fit of the article relative to the body of the wearer.

DETAILED DESCRIPTION OF THE INVENTION

As used herein, the term "absorbent article" refers to devices which absorb and contain body exudates, and more specifically, refers to devices which are placed against or in proximity to the body of the wearer to absorb and contain the vairous exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, bandages and the like.

Figure 1:
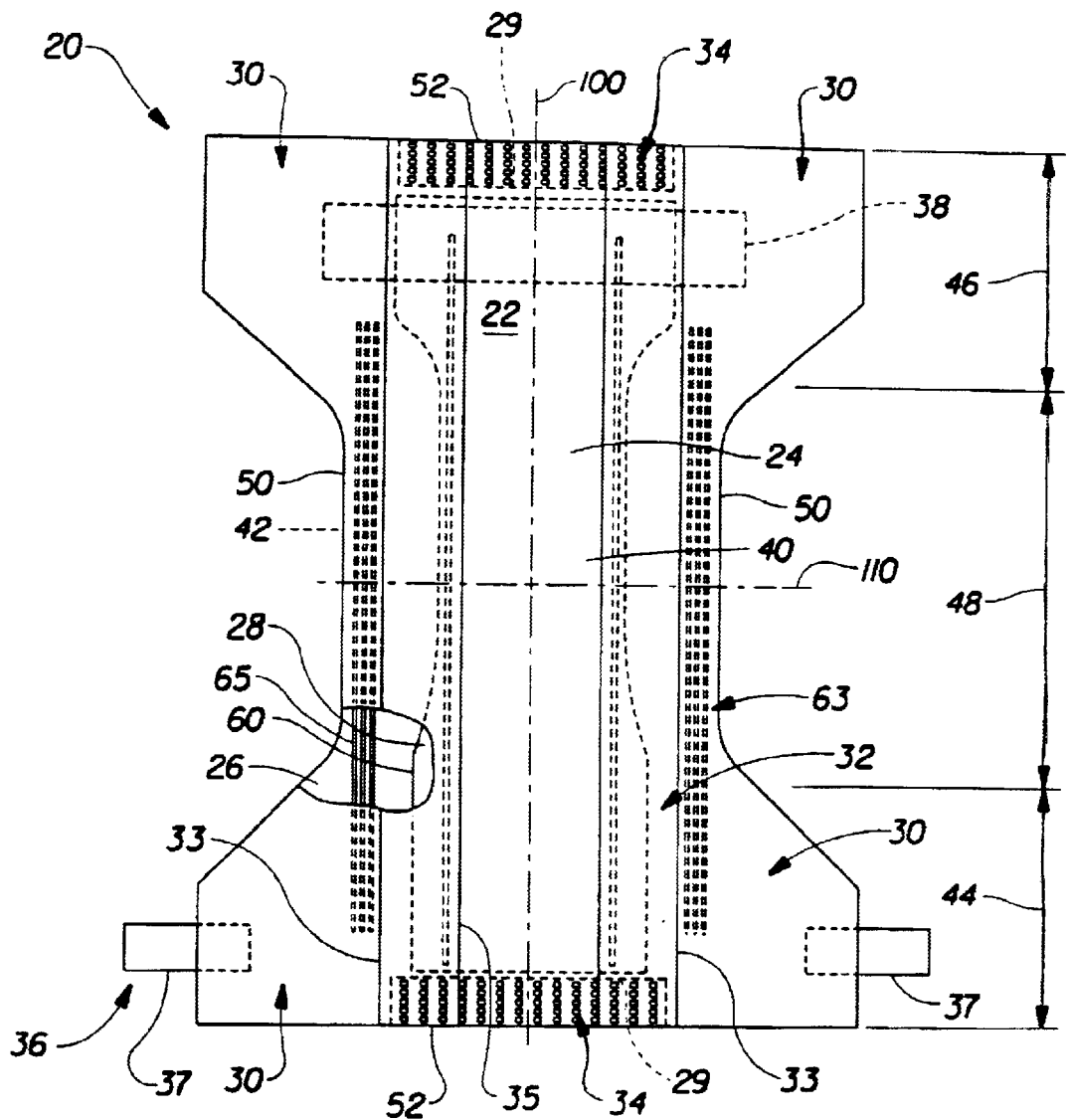
FIG. 1 is a plan view of a disposable absorbent article in accordance with the present invention, in the form of a disposable diaper having a portion of the outer structure cut away to reveal underlying elements, and is shown in its flat condition before the article has been applied to the body of a wearer.

FIG. 1 is a plan view of the diaper 20 of the present invention in a flat-out, state with portions of the structure being cut-away to more clearly show the construction of the diaper 20. The portion of the diaper 20 that faces the wearer is oriented towards the viewer. As shown in FIG. 1, the diaper 20 preferably comprises a liquid pervious topsheet 24; a liquid impervious backsheet 26; an absorbent core 28, which is preferably positioned between at least a portion of the topsheet 24 and the backsheet 26; side panels 30; elasticized leg cuffs 32; an elastic waist feature 34; and a fastening system generally designated 36. Diaper 20 is shown in FIG. 1 to have a first waist region 46, a second waist region 44 opposed to the first waist region 46 and a crotch region 48 located between the first waist region and the second waist region. The periphery of the diaper 20 is defined by the outer edges of the diaper 20 in which the longitudinal side edges 50 run generally parallel to the longitudinal centerline 100 of the diaper 20 and the end edges 52 run between the longitudinal side edges 50 generally parallel to the lateral centerline 110 of the diaper 20.

The chassis 22 of the diaper 20 comprises the main body of the diaper 20. The chassis 22 comprises at least a portion of the absorbent core 28 and preferably an outer covering layer including the topsheet 24 and the backsheet 26. Chassis 22 includes an inner, body-facing surface 40, and an outer, garment-facing surface 42. If the absorbent article comprises a separate holder and a liner, the chassis 22 generally comprises the holder and the liner. For unitary absorbent articles, the chassis 22 comprises the main structure of the diaper with other features added to form the composite diaper structure. While the topsheet 24, the backsheet 26, and the absorbent core 28 may be assembled in a variety of well-known configurations, preferred diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell et al. on Sep. 29, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; U.S. Pat. No. 5,580,411 entitled "Zero Scrap Method For Manufacturing Side Panels For Absorbent Articles" which issued to Nease et al. on Dec. 3, 1996; and U.S. patent application Ser. No. 08/915,471 entitled "Absorbent Article With Multi-Directional Extensible Side Panels" filed Aug. 20, 1997 in the name of Robles et al.; each of which is incorporated herein by reference.

The backsheet 26 is generally that portion of the diaper 20 positioned adjacent the garment-facing surface of the absorbent core 28. Backsheet 26 prevents the exudates absorbed and contained therein from soiling articles that may contact the diaper 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT application Ser. No. WO 95/16746, published on Jun. 22, 1995 in the name of E. I. DuPont and copending U.S. patent application Ser. No. 08/744,487, filed on Nov. 6, 1996 in the name of Curro. Other breathable backsheets including nonwoven webs and apertured formed films are described in U.S. Pat. No. 5,571,096 issued to Dobrin et al. on Nov. 5, 1996. Each of these references is hereby incorporated by reference herein.

The backsheet 26, or any portion thereof, may be elastically extensible in one or more directions. In one embodiment, the backsheet 26 may comprise a structural elastic-like film ("SELF") web. SELF webs suitable for the present invention are more completely described in U.S. Pat. No. 5,518,801 entitled Web Materials Exhibiting Elastic-Like Behavior, which issued to Chappell, et, al. on May 21, 1996, which is incorporated herein by reference. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28, or any other element of the diaper 20 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986, entitled "Disposable Waste-Containment Garment," which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173, issued to Sprague, Jr. on Oct. 7, 1975; U.S. Pat. No. 4,785,996, issued to Ziecker, et al. on Nov. 22, 1978; and U.S. Pat. No. 4,842,666 issued to Werenicz on Jun. 27, 1989. The disclosures of each of those patents is hereby incorporated herein by reference to the same extent as if fully rewritten. Adhesives that have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably positioned adjacent the body-facing surface of the absorbent core 28 and may be joined thereto and/or to the backsheet 26 by any attachment means known in the art. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to other elements of the diaper 20.

The topsheet 24 is preferably compliant, soft feeling, and non-irritating to the wearer's skin. Further, at least a portion of the topsheet 24 is liquid pervious, permitting liquid to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the absorbent assemblies include fibers, the fibers may be spunbonded, carded, wet-laid, meltblown, hydroentangled, or otherwise processed as is known in the art. One suitable topsheet 24 comprising a web of staple length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries," which issued to Thompson on Dec. 30, 1975; U.S. Pat. No. 4,324,246, entitled "Disposable Absorbent Article Having A Stain Resistant Topsheet," which issued to Mullane, et al. on Apr. 13, 1982; U.S. Pat. No. 4,342,314, entitled "Resilient Plastic Web Exhibiting Fiber-Like Properties," which issued to Radel, et al. on Aug. 3, 1982; U.S. Pat. No. 4,463,045, entitled "Macroscopically Expanded Three-Dimensional Plastic Web Exhibiting Non-Glossy Visible Surface and Cloth-Like Tactile Impression," which issued to Ahr, et al. on Jul. 31, 1984; and U.S. Pat. No. 5,006,394, entitled "Multilayer Polymeric Film," which issued to Baird on Apr. 9, 1991. Other suitable topsheets 24 can be made in accordance with U.S. Pat. Nos. 4,609,518 and 4,629,643, which issued to Curro et al. on Sep. 2, 1986, and Dec. 16, 1986, respectively, the disclosures of each of which are hereby incorporated herein by reference to the same extent as if fully rewritten. Such formed films are available from The Procter & Gamble Company of Cincinnati, Ohio as "DRI-WEAVE" and from Tredegar Corporation of Terre Haute, Ind. as "CLIFF-T."

Preferably, the topsheet 24 is made of a hydrophobic material or is treated to be hydrophobic in order to isolate the wearer's skin from liquids contained in the absorbent core 28. If the topsheet 24 is made of a hydrophobic material, preferably at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344, entitled "Absorbent Articles with Multiple Layer Absorbent Layers," which issued to Reising, et al. on Jan. 29, 1991, and U.S. Pat. No. 4,988,345, entitled "Absorbent Articles with Rapid Acquiring Absorbent Cores," which issued to Reising on Jan. 29, 1991. A more detailed discussion of some suitable methods for incorporating surfactant in the topsheet can be found in U.S. Statutory Invention Registration No. H1670, which was published on Jul. 1, 1997, in the names of Aziz et al. The disclosures of each of those references are hereby incorporated herein by reference to the same extent as if fully rewritten.

Alternatively, the topsheet 24 may include an apertured web or film that is hydrophobic. This may be accomplished eliminating the hydrophilizing treatment step from the production process and/or applying a hydrophobic treatment to the topsheet 24, such as a polytetrafluoroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet 24 may be coated with a lotion as is known in the art. Examples of suitable lotions include those described in U.S. Pat. No. 5,607,760, entitled "Disposable Absorbent Article Having A Lotioned Topsheet Containing an Emollient and a Polyol Polyester Immobilizing Agent," which issued to Roe on Mar. 4, 1997; U.S. Pat. No. 5,609,587, entitled "Diaper Having A Lotion Topsheet Comprising A Liquid Polyol Polyester Emollient And An Immobilizing Agent," which issued to Roe on Mar. 11, 1997; U.S. Pat. No. 5,635,191, entitled "Diaper Having A Lotioned Topsheet Containing A Polysiloxane Emollient," which issued to Roe et al. on Jun. 3, 1997; and U.S. Pat. No. 5,643,588, entitled "Diaper Having A Lotioned Topsheet," which issued to Roe et al. on Jul. 1, 1997. The lotion may function alone or in combination with another agent as the hydrophobizing treatment described above. The topsheet may also include or be treated with antibacterial agents, some examples of which are disclosed in PCT Publication No. WO 95/24173 entitled "Absorbent Articles Containing Antibacterial Agents in the Topsheet For Odor Control," which was published on Sep. 14, 1995, in the name of Theresa Johnson. Further, the topsheet 24, the backsheet 26 or any portion of the topsheet or backsheet may be embossed and/or matte finished to provide a more cloth like appearance.

The absorbent core 28 may comprise any absorbent material that is generally compressible, conformable, non-irritating to the wearer's skin, and capable of absorbing and retaining liquids such as urine and other certain body exudates. The absorbent core 28 has longitudinal side edges 60 and end edges 29 and can be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). However, the total absorbent capacity of the absorbent core 28 should be compatible with the design loading and the intended use of the diaper 20.

Exemplary absorbent structures for use as the absorbent assemblies are described in U.S. Pat. No. 4,610,678, entitled "High-Density Absorbent Structures," which issued to Weisman et al. on Sep. 9, 1986; U.S. Pat. No. 4,673,402, entitled "Absorbent Articles With Dual-Layered Cores," which issued to Weisman et al. on Jun. 16, 1987; U.S. Pat. No. 4,834,735, entitled "High Density Absorbent Members Having Lower Density and Lower Basis Weight Acquisition Zones," which issued to Alemany et al. on May 30, 1989; U.S. Pat. No. 4,888,231, entitled "Absorbent Core Having A Dusting Layer," which issued to Angstadt on Dec. 19, 1989; U.S. Pat. No. 5,137,537, entitled "Absorbent Structure Containing Individualized, Polycarboxylic Acid Crosslinked Wood Pulp Cellulose Fibers," which issued to Herron et al. on Aug. 11, 1992; U.S. Pat. No. 5,147,345, entitled "High Efficiency Absorbent Articles For Incontinence Management," which issued to Young et al. on Sep. 15, 1992; U.S. Pat. No. 5,342,338, entitled "Disposable Absorbent Article For Low-Viscosity Fecal Material," issued to Roe on Aug. 30, 1994; U.S. Pat. No. 5,260,345, entitled "Absorbent Foam Materials For Aqueous Body Fluids and Absorbent Articles Containing Such Materials," which issued to DesMarais et al. on Nov. 9, 1993; U.S. Pat. No. 5,387,207, entitled "Thin-Until-Wet Absorbent Foam Materials For Aqueous Body Fluids And Process For Making Same," which issued to Dyer et al. on Feb. 7, 1995; and U.S. Pat. No. 5,625,222, entitled "Absorbent Foam Materials For Aqueous Fluids Made From high Internal Phase Emulsions Having Very High Water-To-Oil Ratios," which issued to DesMarais et al. on Jul. 22, 1997. The disclosures of each of those patents is hereby incorporated herein by reference to the same extent as if fully rewritten.

The diaper 20 may also comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge 29 of the absorbent core 28 and generally forms at least a portion of the end edge 52 of the diaper 20. Disposable diapers are often constructed so as to have two elastic waist features, one positioned in the first waist region 46 and one positioned in the second waist region 44. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24.

The elastic waist feature 34 may be constructed in a number of different configurations including those described in U.S. Pat. No. 4,515,595, which issued to Kievit et al. on May 7, 1985; U.S. Pat. No. 4,710,189, which issued to Lasch on Dec. 1, 1987; U.S. Pat. No. 5,151,092, which issued to Buell on Sep. 9, 1992; and U.S. Pat. No. 5,221,274, which issued to Buell on Jun. 22, 1993. Other suitable waist configurations may include waistcap features such as those described in U.S. Pat. No. 5,026,364, which issued to Robertson on Jun. 25, 1991 and U.S. Pat. No. 4,816,025, which issued to Foreman on Mar. 28, 1989. The disclosures of each of the above-identified references are incorporated herein by reference to the same extent as if fully rewritten.

The diaper 20 includes a fastening system 36. The fastening system 36 preferably maintains the side panels 30 of the first waist region 46 and the second waist region 44 in at least partially overlapped condition to provide lateral tensions about the circumference of the diaper 20 when it is worn, to hold the diaper 20 on the wearer. In alternative embodiments, opposing sides of the garment may be seamed or welded to form a pant. This allows the article to be used as a pull-on type diaper, such as a training pant.

The fastening system 36 preferably comprises securement members 37 that can be in the form of tape tabs that engage a landing member 38, and/or hook and loop fastening components, although any other known fastening means are generally acceptable. Some exemplary fastening systems are disclosed in U.S. Pat. No. 3,848,594, entitled "Tape Fastening System for Disposable Diaper," which issued to Buell on Nov. 19, 1974; U.S. Pat. No. 4,662,875, entitled "Absorbent Article," which issued to Hirotsu et al. on May 5, 1987; U.S. Pat. No. 4,846,815, entitled "Disposable Diaper Having An Improved Fastening Device," which issued to Scripps on Jul. 11, 1989; U.S. Pat. No. 4,894,060, entitled "Disposable Diaper With Improved Hook Fastener Portion," which issued to Nestegard on Jan. 16, 1990; U.S. Pat. No. 4,946,527, entitled "Pressure-Sensitive Adhesive Fastener And Method of Making Same," which issued to Battrell on Aug. 7, 1990; and the hereinbefore-referenced U.S. Pat. No. 5,151,092, issued to Buell on Sep. 29, 1992; and U.S. Pat. No. 5,221,274, which issued to Buell on Jun. 22, 1993. Other fastening systems are described in more detail in U.S. Pat. Nos. 5,595,567 issued to King et al. on Jan. 21, 1997 and 5,624,427 issued to Bergman et al. on Apr. 29, 1997, both of which are entitled "Nonwoven Female Component For Refastenable Fastening Device." Yet other fastening systems are described in U.S. Pat. Nos. 5,735,840 and 5,928,212, both of which issued to Kline et al. and are entitled "Disposable Diaper With Integral Backsheet Landing Zone." The fastening system may also provide a means for holding the article in a disposal configuration as disclosed in U.S. Pat. No. 4,963,140, which issued to Robertson et al. on Oct. 16, 1990. The disclosures of each of those patents are hereby incorporated herein by reference.

The diaper 20 may also comprise side panels 30. While the diaper 20 of the present invention preferably has the side panels 30 disposed in the second waist region 44, the diaper 20 may be provided with side panels 30 disposed in the first waist region 46 or in both the first waist region 46 and the second waist region 44. The side panels 30 may be constructed in any suitable configurations and may be extensible, elastomeric, or nonextensible. Examples of diapers with elasticized side panels are disclosed in U.S. Pat. No. 4,857,067, entitled "Disposable Diaper Having Shirred Ears," which issued to Wood, et al. on Aug. 15, 1989; U.S. Pat. No. 4,381,781, which issued to Sciaraffa, et al. on May 3, 1983; U.S. Pat. No. 4,938,753, which issued to Van Gompel, et al. on Jul. 3, 1990; the hereinbefore-referenced U.S. Pat. No. 5,151,092, which issued to Buell on Sep. 29, 1992; U.S. Pat. No. 5,221,274, which issued to Buell on Jun. 22, 1993; U.S. Pat. No. 5,669,897, entitled "Absorbent Articles Providing Sustained Dynamic Fit," which issued to LaVon, et al. on Sep. 23, 1997; U.S. Patent application Ser. No. 08/155,048, entitled "Absorbent Article With Multi-Directional Extensible Side Panels," filed Nov. 19, 1993, in the names of Robles, et al. The disclosures of each of the foregoing patents are hereby incorporated herein by reference to the same extent as if fully rewritten.

The diaper 20 preferably further includes leg cuffs 32 that provide improved containment of liquids and other body exudates. Leg cuffs may also be referred to as leg bands, side flaps, barrier cuffs, or elastic cuffs. U.S. Pat. No. 3,860,003 describes a disposable diaper that provides a contractible leg opening having a side flap and one or more elastic members to provide an elasticized leg cuff (a gasketing cuff). U.S. Pat. Nos. 4,808,178 and 4,909,803, issued to Aziz et al. on Feb. 28, 1989, and Mar. 20, 1990, respectively, describe disposable diapers having "stand-up" elasticized flaps (barrier cuffs) which improve the containment of the leg regions. U.S. Pat. Nos. 4,695,278 and 4,795,454, issued to Lawson on Sep. 22, 1987, and to Dragoo on Jan. 3, 1989, respectively, describe disposable diapers having dual cuffs, including gasketing cuffs and barrier cuffs. In some embodiments, it may be desirable to treat all or a portion of the leg cuffs with a lotion, as described above. In addition to leg cuffs 32, diaper 20 can also include an elastic gasketing cuff 63 with one or more elastic strands 65 positioned outboard of the barrier cuff.

Figure 2:
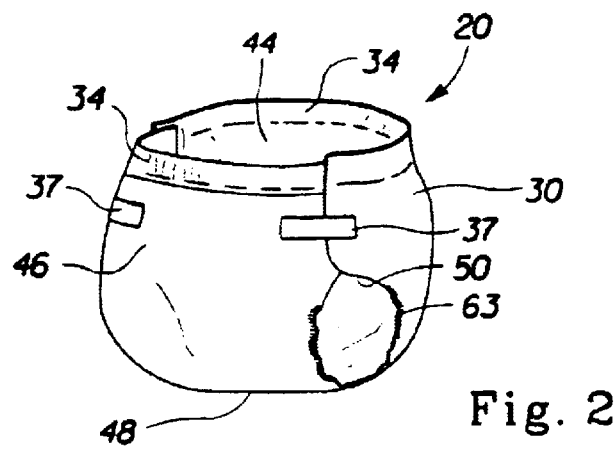
FIG. 2 is a perspective view of a disposable absorbent article in accordance with the present invention in its assembled condition, as it is worn by a wearer.

Diaper 20 is shown in assembled form in FIG. 2. When assembled and on the body of the wearer, crotch region 48 is against the wearer's crotch, rear waist region 44 is against the wearer's lower back adjacent the wearer's waist, and front waist region 46 overlies the wearer's stomach. Respective securement members 37, in the form of fastener tabs, have been attached to front waist region 46 to hold the diaper in assembled form about the wearer's lower torso until such time as it is necessary to remove the diaper, which is effected by removing the fastener tabs from front waist region 46. It should be noted that the diaper 20 may be configured such that the securement elements 37 are attached to the rear waist region 44 during use rather than the front waist region 46. Further, the use of the terms "front" and "rear" with respect to waist regions are interchangeable and should not be construed as limiting the present invention.

When diaper 20 is in its assembled form, as shown in FIG. 2, longitudinally extending side edges 50 define leg openings that encircle the wearer's thighs to prevent leakage therearound. Elastic gasketing cuffs 63 can provide a further sealing effect around the wearer's thighs to prevent leakage. It will be apparent that side edges 50 are preferably in contact with the wearer's thighs, and the extent of that contact and the contact pressure are determined by the orientation of diaper 20 on the body of the wearer and the orientation of fastener tabs 37 relative to the diaper longitudinal centerline. Thus, if fastener tabs 37 are each placed at significantly different distances from longitudinal centerline 100 (see FIG. 1) of diaper 20, the diaper will not be symmetrically positioned on the wearer's body, and therefore one of the leg openings will be larger than the other. If side edge 50 that defines the smaller leg opening is in contact with the entire periphery of the wearer's thigh, without undue pressure thereon, then the other leg opening likely is too loose, possibly permitting undesirable leakage. If side edge 50 that defines the smaller leg opening is too loose, and defines a leg opening that is too large, then the other leg opening, which is even larger, will also be too loose. But if the smaller leg opening is too tight, and the larger leg opening is in contact with the entire periphery of the wearer's thigh, then although it is unlikely that there will be leakage, the wearer will experience discomfort from the tightness of the smaller leg opening. By providing and utilizing the indicia in accordance with the present invention, however, the problems noted above as well as others resulting from an ill-fitting diaper can be minimized.

One embodiment of a diaper in accordance with the present invention preferably includes a front waist area that carries a first indicium for facilitating proper positioning of securement members, which can be in the form of fastener tabs, as shown, and wherein the fastener tabs each carry a second indicium. The second indicium preferably relates to and complements the first indicium, to serve as a visual aid in positioning the side panels or fastener tabs symmetrically on the front waist area of the diaper, relative to the diaper longitudinal centerline.

Figure 3:
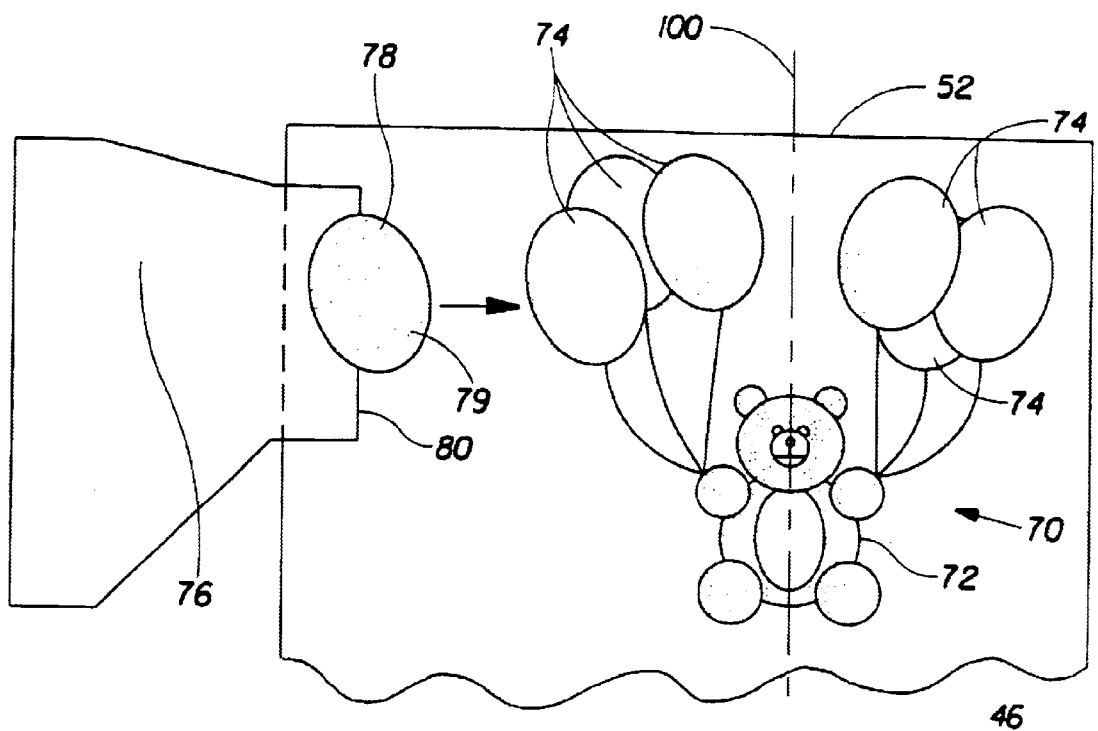
FIG. 3 is an enlarged, fragmentary view of a portion of a waist area and one fastener tab of a disposable absorbent article in accordance with the present invention showing one form of position-facilitating indicia.

Referring to FIG. 3, there is shown one embodiment of a diaper fastener positioning arrangement in accordance with the present invention. The outwardly-facing surface of the chassis includes an ornamental design, or first indicium 70, in the form of a predetermined visual image that is positioned on front waist region 46 and that is adjacent front waist end edge 52. (It should be noted that the visual image, e.g., first indicia 79 may be disposed directly or indirectly on the backsheet 26 or any other part of the outer cover of the diaper or may be part of a landing zone member which is joined to the backsheet 26 or other part of the chassis.) As shown, first indicium 70 includes several design elements that are substantially the same and that are positioned in mirror image form on respective sides of diaper longitudinal centerline 100. If desired, first indicium 70 can be positioned on front waist region 46 in a symmetrical manner, relative to longitudinal centerline 100. Thus, in first indicium 70 illustrated in FIG. 3, a teddy bear 72 is shown to be carrying two groups of balloons 74 that are held in the bear's hands. The two groups of balloons 74 shown are preferably symmetrically positioned, relative to longitudinal centerline 100. Bear 72 can also be symmetrically positioned on longitudinal centerline 100, if desired.

Side panels 76, only one of which is shown in FIG. 3, can each include at least one securement member 79. The side panels 76, securement members 79 or both may include a second indicium element 78 in the form of a predetermined visual image that is visually related to or that is complementary with one or more elements of the ornamental design of first indicium 70. In that connection, as used herein with respect to indicia the terms "complement" or "complementary" refer to a visual image or to a shape that completes an incomplete visual image, or that integrates with another visual image so as to be seen to be a part of that other image or to be visually related thereto. Thus, as shown in FIG. 3, side panel 76 and securement member 79 together include a second indicium element 78 in the form of a balloon, which can be substantially the size and shape of at least one of the balloons included in first indicium 70 to facilitate the mental association of the first and second indicia. (Of course, the first indicium 70 and second indicium 78 can include any visual or image or shape so long as they are complementary, as described above.) First indicium 70 is preferably positioned, generally on the backsheet outer surface or on a landing zone member joined to the backsheet so that at least one of the balloons on each side of longitudinal centerline 100 underlies a respective side panel 76 and/or securement element 79 when the diaper is placed on the body of the wearer and is in its wearing position, so that balloon element 78 appears to be an integral part of first indicium 70 when the diaper is worn. However, it is not essential that second indicium element 78 overlie a part of first indicium 70, and indicia can be selected wherein no overlap of the first and second indicia occurs, if desired.

In FIG. 3, the balloons that form part of first indicium 70 serve as orientation and possible positioning points for attachment of the securement members 79, so that the points at which each securement member 79 is secured to front waist region 46 are spaced substantially equally from longitudinal centerline 100. Application of the securement members 79 in that manner will preferably result in symmetry of the diaper relative to the wearer's body, with resulting correct fit of the diaper to avoid excessive gapping at the leg openings, such as could occur if the securement members 79 were not attached substantially equidistant from centerline 100.

As is apparent from FIG. 3, the balloon extends beyond outermost edge 80 of the side panel 76. In that regard, the indicia can be attachments that are removably or non-removably secured to the respective side panels 76 or securement members 79 or, alternatively, they can be an integral part of either or both elements.

Figure 4:
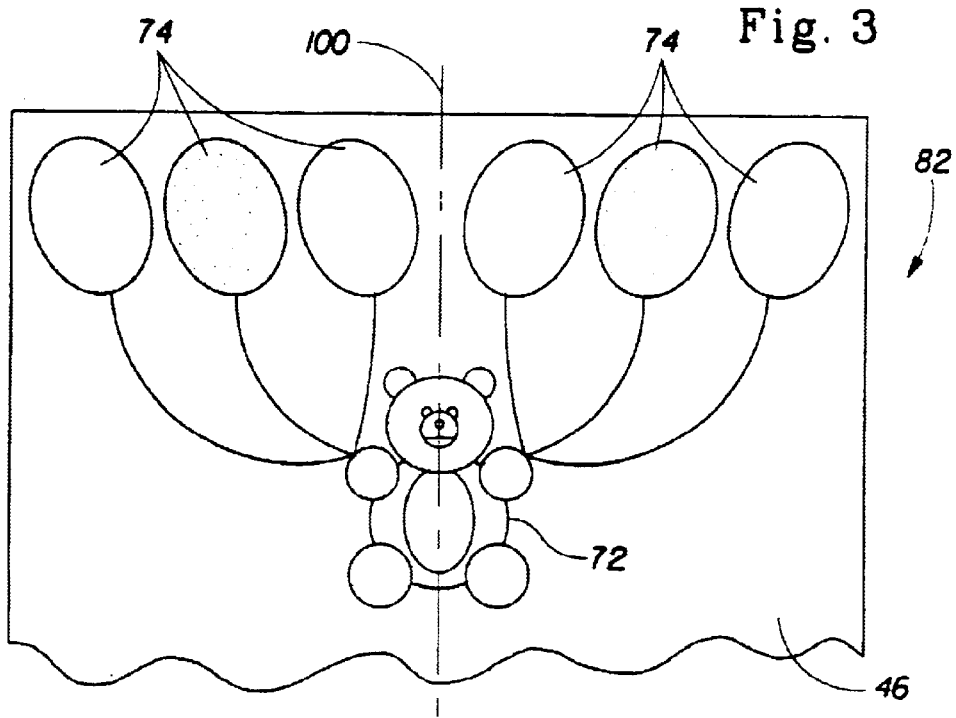
FIG. 4 is a view similar to that of FIG. 3, showing another form of a waist area position-facilitating indicium.

Another arrangement of a first indicium 82 that includes an interactive design is shown in FIG. 4. As shown, balloons 74 are of substantially equal size and are laterally aligned in two groups, one group on each side of and spaced generally symmetrically relative to longitudinal centerline 100, to define a band of balloons that extends substantially perpendicularly relative to longitudinal centerline 100. The complementary side panels or securement members can have the structure and appearance of those shown in FIG. 3, so that the applier of the diaperer can during application substantially align the balloons on the fastener tabs with the band of balloons on front waist region 46. Again, the side panels are preferably fastened symmetrically, relative to first indicium 82, which is preferably positioned on longitudinal centerline 100 to enable optimum fit of the diaper.

Figure 5:
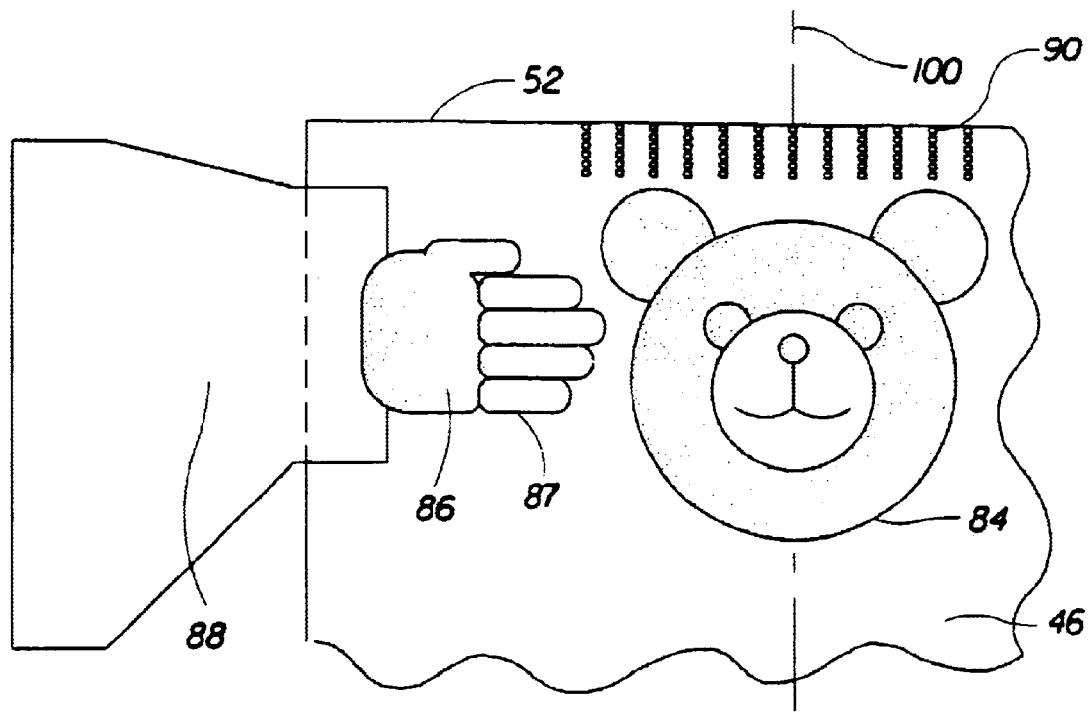
FIG. 5 is a view similar to that of FIG. 3, showing a further form of a waist area position-facilitating indicium and also another form of fastener tab, before the tab has been placed in diaper-securing position.
Figure 6:
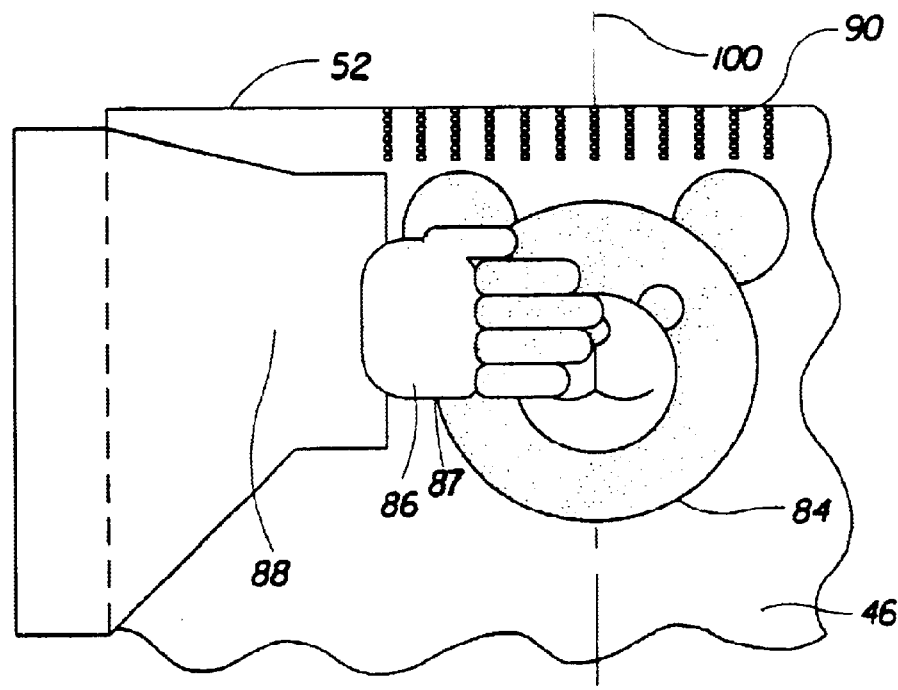
FIG. 6 is a view of the indicia of FIG. 5 after the fastener tab has been placed in diaper-securing position.

In addition to a multi-element first indicium, such as those shown in FIGS. 3 and 4, the first indicium can, if desired, be a unitary and complete visual image 84, such as that shown in FIGS. 5 and 6. Although any unitary visual image can be used, the image is preferably a symmetrical design and is symmetrically positioned is relative to and in overlying relationship with longitudinal centerline 100. Complementary second indicium 87, in this instance a bear paw, is carried by fastener tabs 86 (only one of which is shown in FIGS. 5 and 6), and it is adapted to overlie a portion of first indicium 84 in such a manner that it is visually apparent to the person applying the diaper how to position and attach the respective fastener tabs to enable proper fit of the diaper to the body of the wearer. Optionally, a secondary positioning indicium 90, such as the parallel strips of longitudinally-aligned dots or circles shown in FIGS. 5 and 6, can be placed on the backsheet adjacent to end edge 52 in the event first indicium 84 is desired to be supplemented to provide an additional visual guide for lateral and longitudinal positioning of the tabs. FIG. 5 shows the elements of this embodiment before placement of the fastener tab 86 onto the backsheet or landing zone, and FIG. 6 shows one of the possible relative positions of the elements after attachment of the fastener tabs.

Figure 7:
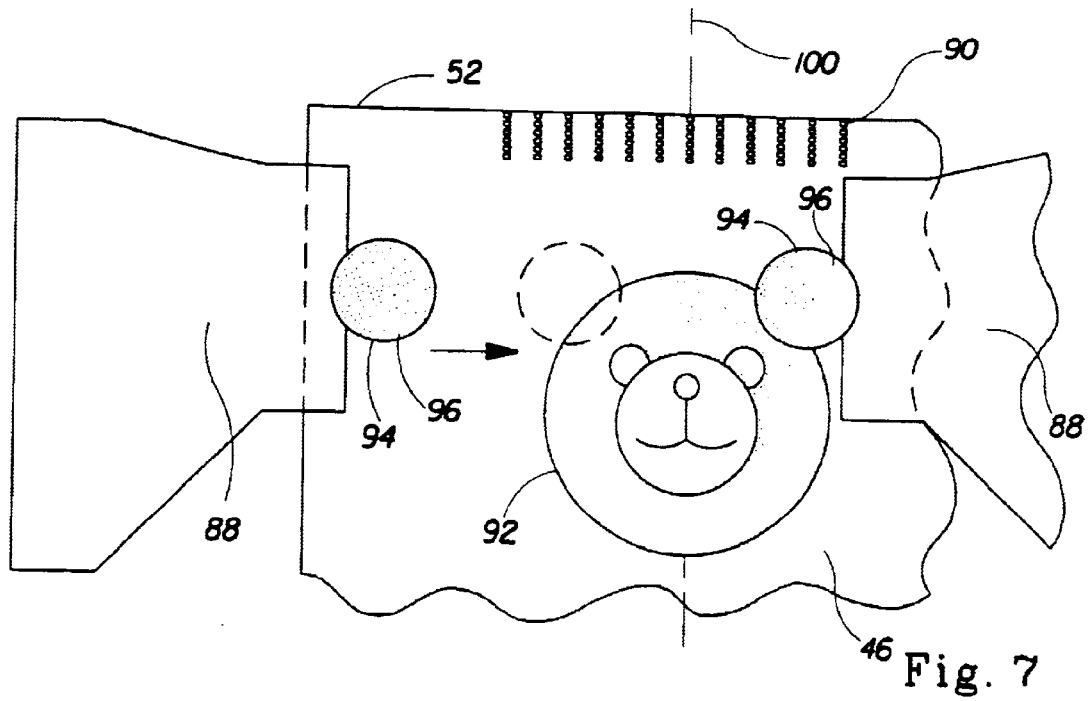
FIG. 7 is view similar to that of FIG. 5, showing a still further form of position-facilitating indicia.

An alternative embodiment of the present invention is shown in FIG. 7, in which a first indicium 92 is an incomplete visual representation of a particular and familiar design, for example a face of a well-known cartoon character, or the like. First indicium 92 is preferably positioned symmetrically with and in overlying relationship with longitudinal centerline 100. The missing elements of the visual image, in this instance a visual representation corresponding substantially with a teddy bear's ears, are carried as the second indicia 94 by each of fastener tabs 96. When tabs 96 are fastened in position symmetrically on the surface of the landing zone of backsheet 46, second indicia 94 carried by tabs 96 join with the incomplete first indicium to substantially complete the intended overall visual image.

Figure 8:
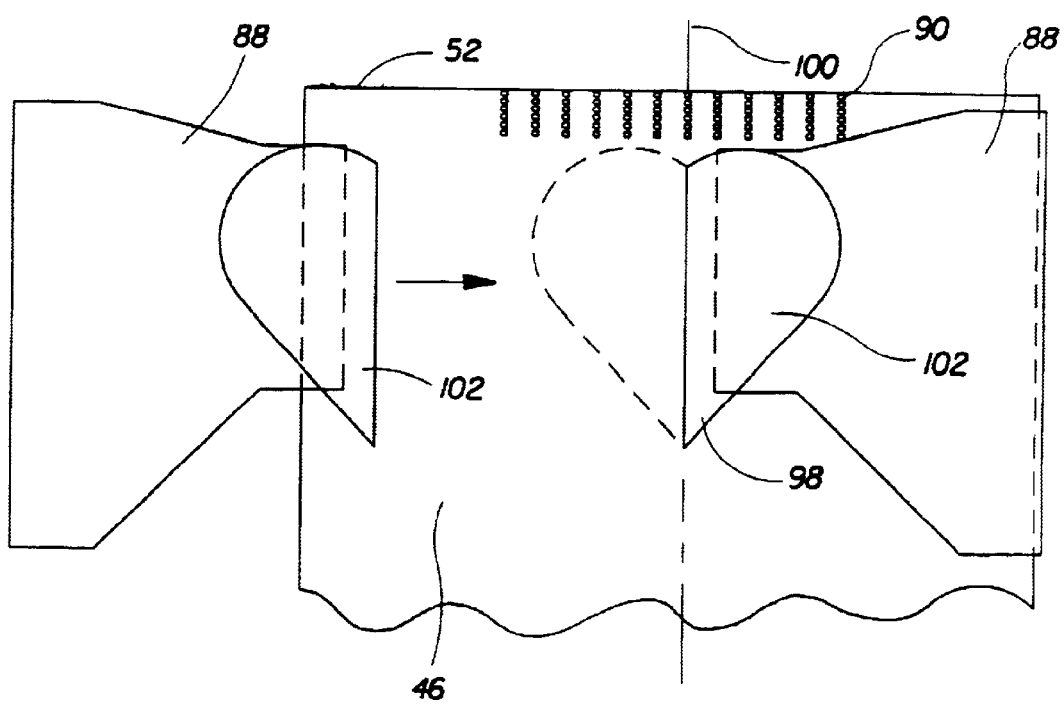
FIGS. 8 and 8A are views similar to that of FIG. 5, showing different forms of fastener tabs having a tab-position-facilitating indicium.
Figure 8A:
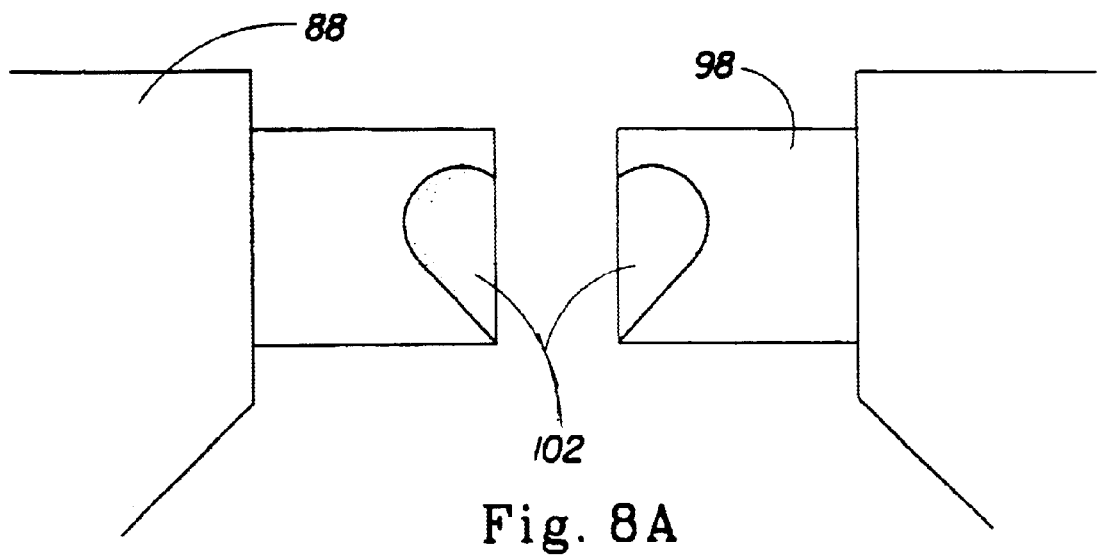
Figure 9:
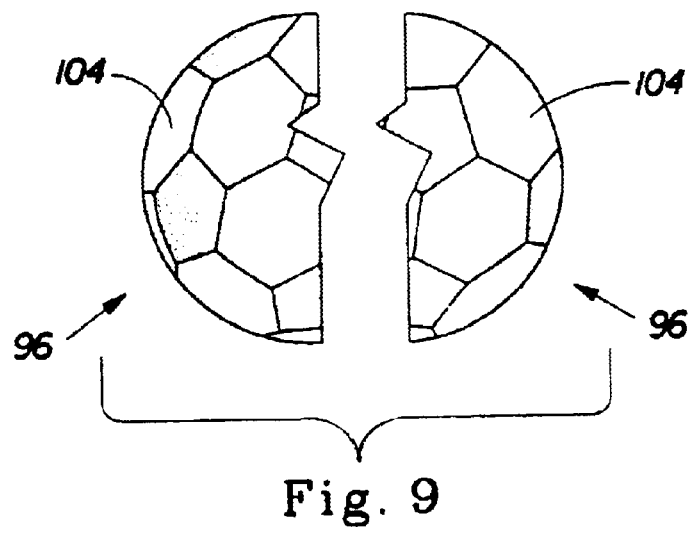
FIG. 9 is a view similar to that of FIG. 8, showing a further form of a fastener tab having a position-facilitating indicium.

Another form of second indicium carried by the fastener tabs for facilitating symmetrical positioning of the tabs is shown in FIGS. 8, 8A and 9. Referring first to FIGS. 8 and 8A, each fastener tab 98 includes one-half of a familiar visual image 102, in this instance a heart. In the embodiment shown in FIG. 8, the fastener tab 98 is shaped to make up one half of the visual image 102, whereas in the embodiment shown in FIG. 8A, the visual image 102 is shown as an image located on at least a portion of the fastener tab 98. (As with any of the other embodiments described herein, the visual image 102 or indicia may be disposed on the side panels 88 of the diaper along with or rather than being disposed on the fastening tabs 98.) If the fastener tabs 98 (or side panels 88) are properly and symmetrically positioned on the diaper, they will substantially complete the overall image of the heart. As in the embodiment shown in FIG. 8, an optional secondary positioning indicium 90 can be provided in addition, if desired.

The FIG. 9 embodiment is similar to the FIG. 8 embodiment in that the fastener tabs 96 each include visual images 104 which, when properly positioned on the diaper, define a substantially complete design element, in this instance a soccer ball.

Figure 10:
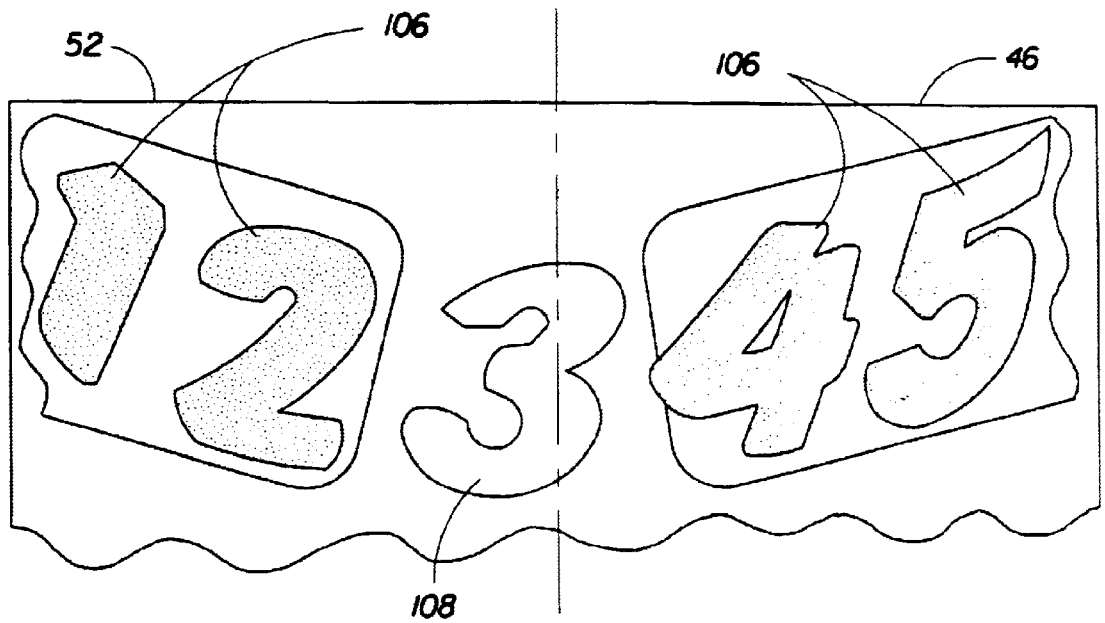
FIG. 10 is a view similar to that of FIG. 3, showing another form of a waist area position-facilitating indicium and side panels having indicia that are complementary to the waist area indicium.
Figure 11:
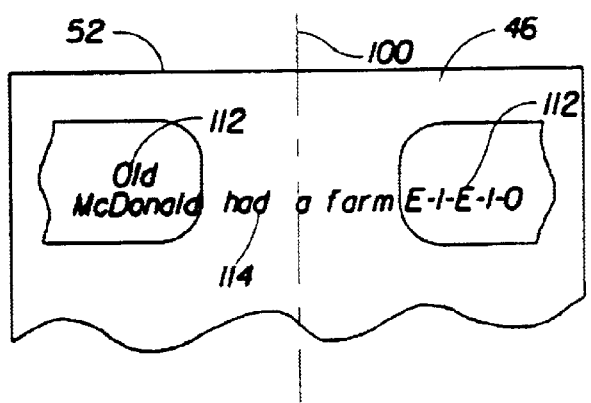
FIG. 11 is a view similar to that of FIG. 10, showing a further form of a waist area position-facilitating indicium and side panels having indicia that are complementary to the waist area indicium.

Still further embodiments of the present invention, involving alphabetical and numerical visual elements, are shown in FIGS. 10 and 11. In FIG. 10 second indicia elements 106 can define respective portions of a numerical progression that are complete when positioned properly on the diaper or may provide a progression that is missing a number or numbers that logically should be within the progression. First indicia can include, for example, the missing number 108 which can be provided on the backsheet or landing zone of the diaper. Preferably the first indicia is positioned substantially symmetrically relative to and overlying longitudinal centerline 100, and at a predetermined distance from front waist end edge 52 of the diaper.

FIG. 11 shows verbal tab indicia 112 that are fragments of a word or familiar series of words, and that cooperate with a verbal indicium 114 on the diaper. Verbal indicium 114 is also a fragment of that same word or familiar series of words. Both verbal indicia 112 and verbal indicia 114, when positioned as shown combine to complete a word or familiar phrase. In this instance some of the words to the well-known child's song, "Old McDonald Had a Farm" are shown. Again, verbal indicium 114 is preferably positioned at a predetermined location to enable proper fit of the assembled diaper to the body of the wearer.

Figure 12:
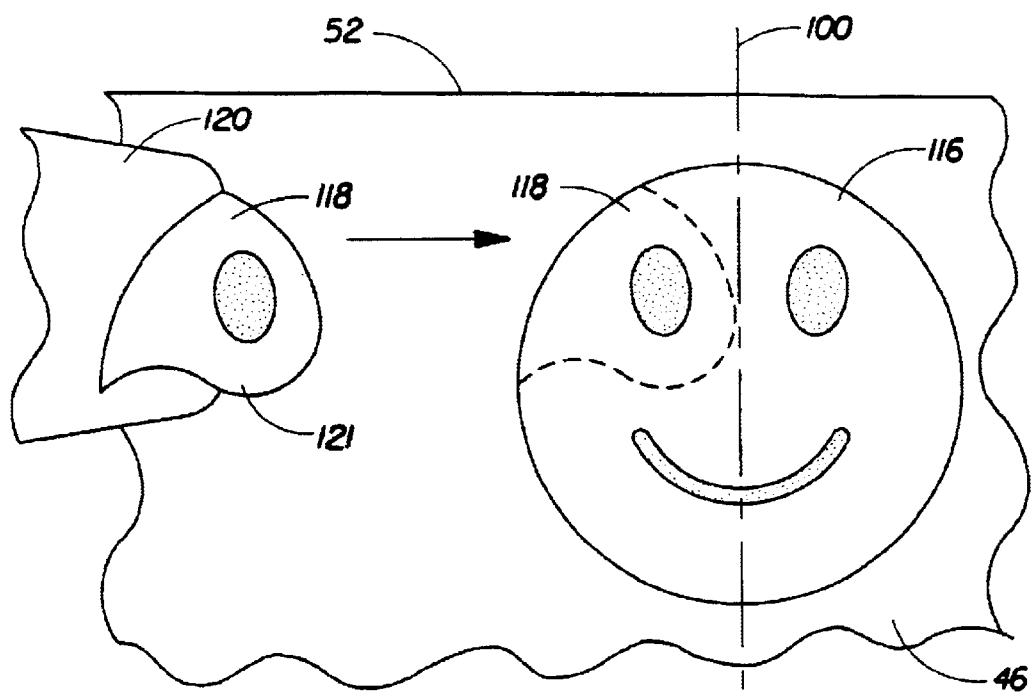
FIG. 12 is a view similar to that of FIG. 5, showing another form of a waist area position-facilitating indicium and a fastener tab having corresponding indicia to overlie the waist area indicium.

Another embodiment of the present invention is shown in FIG. 12. As shown, a complete visual image for a first indicium 116 is preferably positioned on a portion of the backsheet or landing zone. A second indicium 118 is carried by side panel 120 and/or fastener 121. Second indicium 118 preferably corresponds with a portion of first indicium 116 and overlies a part of first indicium 116 and is complementary therewith to define a predetermined visual image when the fasteners are properly and symmetrically applied to the diaper.

Figure 13:
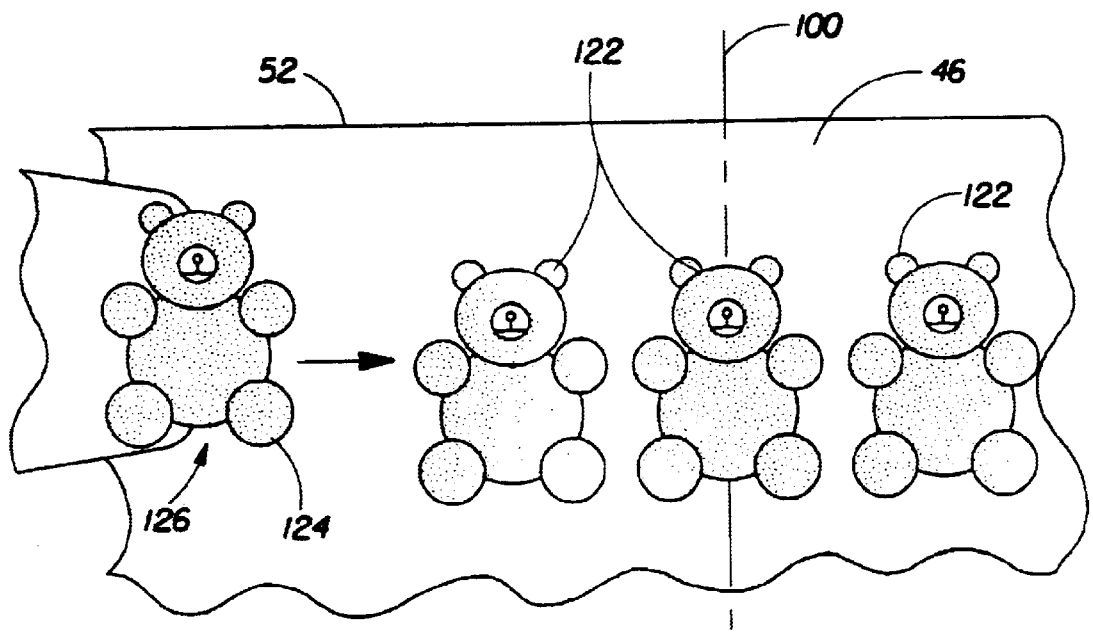
FIG. 13 is a view similar to that of FIG. 5, showing a still further form of a waist area position-facilitating indicium and a fastener tab having corresponding indicia.

A still further embodiment of the present invention is shown in FIG. 13. In that embodiment, the first indicium 122 includes several repetitive, generally laterally aligned visual images that are positioned at a desired distance from, for example, the front waist end edge 52 of the diaper. Second indicia 124 are carried by each of the fastener tabs (only one of which is shown). Each of the second indicia 124 may be substantially identical with the visual images defining first indicium 122, to enable an applier to properly position fastener tabs 126 on the diaper 46 for proper fit of the diaper.

Figure 14:
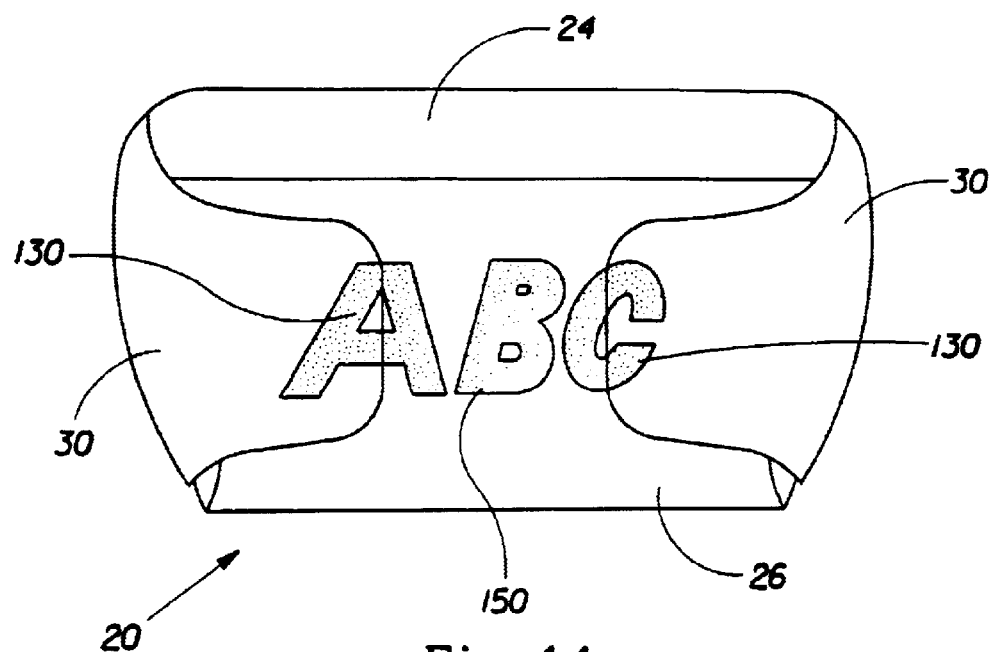
FIG. 14 is an alternative embodiment of the present invention wherein the position-facilitating indicium is used to help configure the diaper for proper disposal.

Yet another embodiment of the present invention is shown in FIG. 14. In FIG. 14, the diaper is shown in a disposal configuration. The disposal configuration is generally the configuration in which the diaper 20 is rolled-up and fastened in such a way that the diaper 20 can be disposed of (e.g. thrown into the trash or placed into a used diaper receptacle) without leaking any significant amount of fecal matter which may be held in the diaper 20. As shown in the Figure, the side panels 30 of the diaper 20 can be wrapped around the diaper 20 after it has been rolled-up. The side panels or any fastening tabs may be fastened to the backsheet or outer cover of the diaper 20 or to designated disposal fastening elements which may be joined or located on the outer cover of the diaper. In order to help the user to determine where the side panels or fastening tabs should be located during disposal, the diaper 20 of the present invention may include one or more disposal indicium elements 150 located on the outer cover of the diaper 20. The disposal indicium elements 150 may include any of the indicium element types described herein with respect to the fastening system used to apply and position the diaper 20 about the wearer for normal use. Further, the disposal indicium elements 150 may be located in the front waist region, the rear waist region and/or the crotch region of the diaper 20. As with the fastening systems described above, the disposal indicium elements 150 may be related to or complementary with one or more of the indicium elements 130 located on the side panels 30 or fastener tabs and may add to, complete or modify the visual image of the disposal indicium elements 150. Further, the indicium elements 130 of the side panels 30 or fastener tabs for use with the disposal indicium elements 150 may be the same as or different from the indicium elements used to fasten the diaper 20 when worn.

Figure 15:
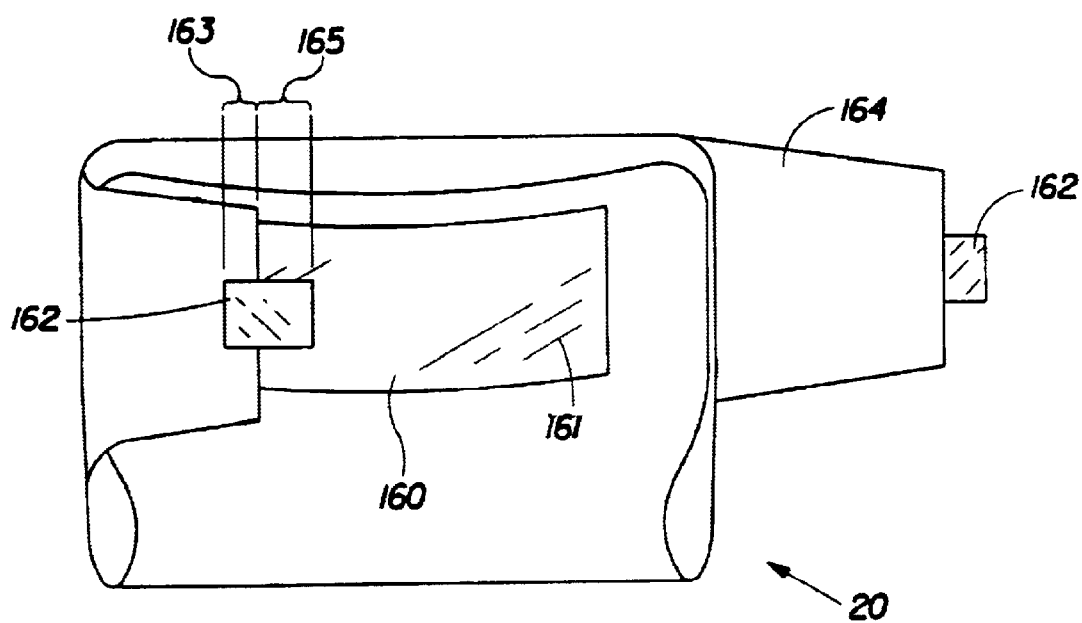
FIG. 15 shows a partial view of an alternative embodiment of the present invention where at least a portion of the fastening tab is translucent.

FIG. 15 shows one embodiment of an alternative construction of the absorbent article 20 of the present invention. In this embodiment, the diaper includes a landing zone 160 to which the fastening tabs 162 can be fastened. The landing zone may be of any size or shape and may be integral with the backsheet or any other part of the diaper or may be a separate element joined to the diaper. In any case, at least a portion of the landing zone 160 includes a first color 161. At least a portion of the fastener tabs 162, or side panels 164 are preferably translucent, and more preferably generally transparent such that the landing zone 160 can be seen through the fastener tab 162 and/or side panel 164 when the diaper is attached about the wearer. The translucent or transparent fastener tabs 162 or side panels 164 preferably includes a second color 163. In a preferred embodiment, when the translucent or transparent fastener tabs 162 or side panels 164 are placed over the portion of the landing zone 160 including the first color 161, a resulting color 165 which is different from the first color 161 or the second color 163 is visible. The landing zone 160 or any portion of the tabs 163 or side panels 164 may include different areas with different colors to provide a system for identifying particular fit parameters for the diaper. Thus, the diaperer can be directed to place the tabs 163 and/or side panels 164 in such a way to provide a particular resulting color 165 in order to provide a certain fit for the wearer, or for disposal.

Figure 16:
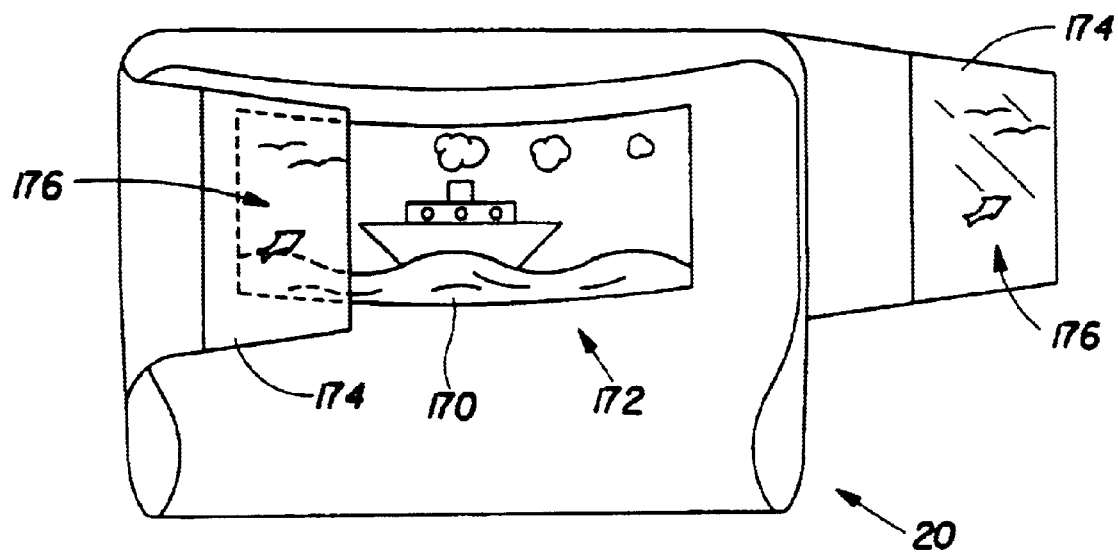
FIG. 16 shows a partial view of an alternative embodiment of the present invention where at least a portion of the side panel is transparent and includes position-facilitating indicia.
Figure 3:
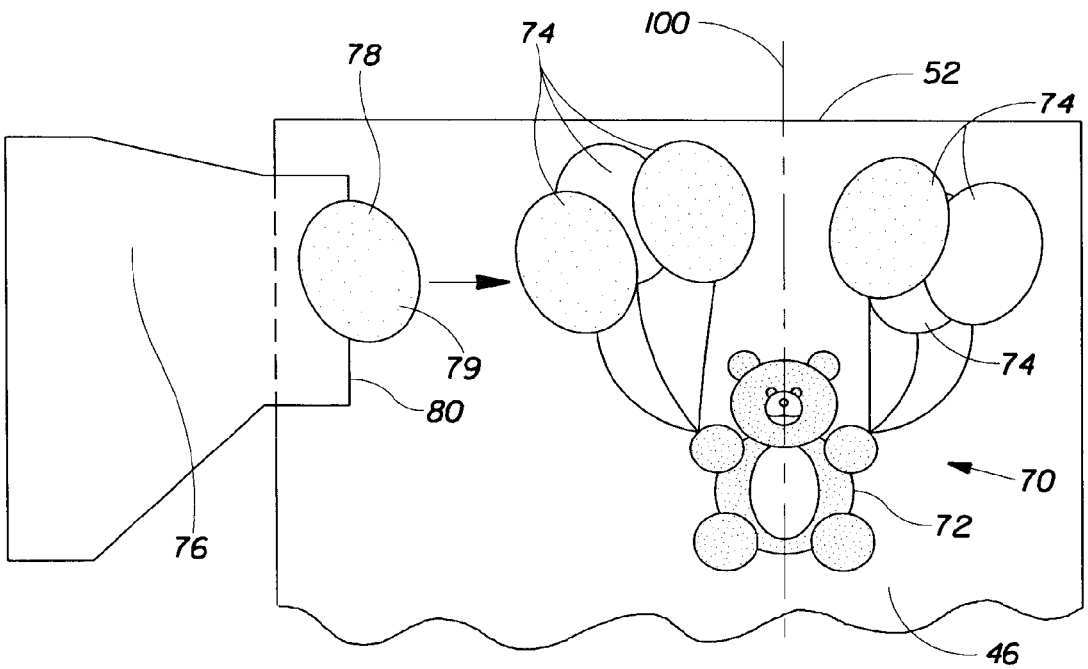
Figure 4:
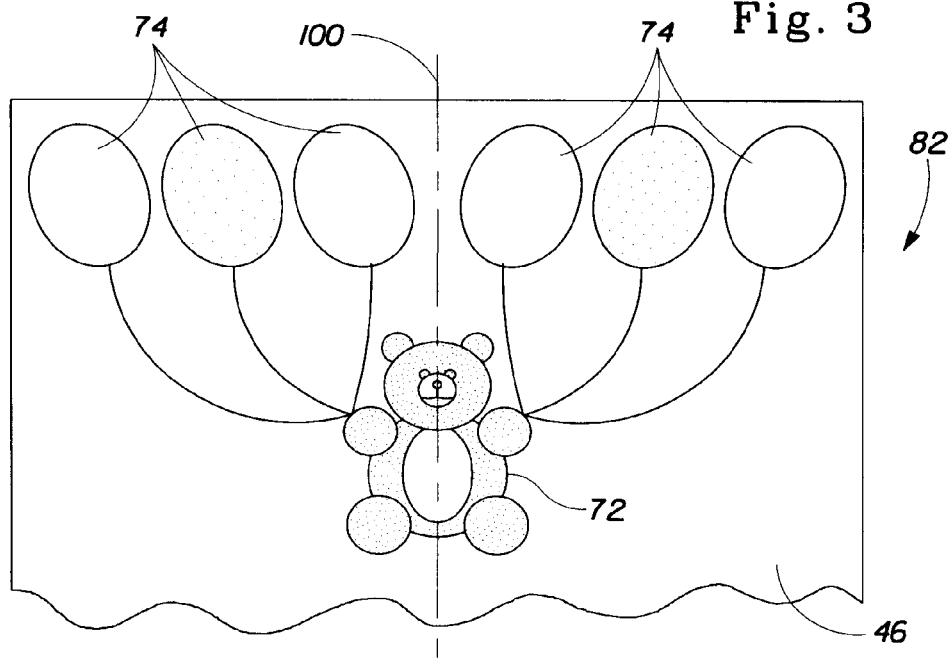

In FIG. 16, yet another embodiment of the present invention is shown wherein the diaper includes a landing zone 170 including first indicia 172. In this example, first indicia 172 comprises a scene including a ship and water, although any suitable indicia may be used. The side panels 174 or fastening tabs include portions which are transparent or translucent (i.e. see-through) as well as second indicia 176, in this case birds and a dolphin. The fastening tabs or side panels 174 have see-through portions so that the user can see the landing zone first indicia 172 beneath the side panel or fastening tab when the diaper is fastened about the wearer. The second indicia 176 are intended to complement the visual image of the first indicia 172 when the diaper is fastened. Accordingly, as shown in FIG. 16, when the side panel 174 is positioned over the landing zone 170, the boat and water scene shows through the see-through portion of the side panel 174 and the second indicia 176 appear to become part of the same image. The first and second indicia can be arranged in a way that helps the user determine the proper fastening position for the fastener or side panel, or to help the user determine the proper configuration for disposal.

As noted in some of the above examples, in addition to providing second indicium elements as particular shapes of fastener tabs or as particular visual images carried by the fastener tabs, if desired in any of the embodiments of the present invention, the second indicium elements can be carried by or applied to the diaper side panels 30. Thus, each of diaper side panels 30 can carry appropriate second indicium elements that can be associated with a predetermined first indicium element that is carried on the outer surface of the diaper, to assist in the desired positioning of the diaper on the body of the wearer. Moreover, the present invention can also be utilized in diaper structures that do not include fastening elements in the form of tape or mechanical fastening tabs as shown in the drawings, but that include forms of fastening elements that are different from the conventional tape tabs as illustrated herein, including, but not limited to, diaper side panels that include attached fastening devices or that include integrally-formed fastening devices. Finally, the indicia that form parts of the present invention can be provided in the form of surface printing, decals applied to the diaper, embossments or texturing of respective surfaces of the diaper, attachments to the surfaces of the diaper, raised elements extending out from the surface of the diaper and the like.

Although particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. In that regard, numerous different design elements can be conceived and utilized to serve as the first and second indicia referred to herein. Therefore, the appended claims are intended to cover all such changes and modifications that are within the scope of this invention.

What is claimed is:

1. A disposable absorbent article comprising:
   (a) a chassis having a tongitudinal central axis and a garment-feting surface and a body-facing surface, the chassis adapted to extend front a back waist area of a wearer to a front waist area of a wearer with the body-facing surface overlying a crotch area of the wearer, the chassis including a first waist region, a second waist region and a crotch region;
   (b) a pair of side panels extending substantially laterally outwardly from respective edge portions of the second waist region of the article, the side panels each having an ornamental shape, carrying a securement element for engagement with a landing zone located on the garment-facing surface at the first waist region of the article for securing the article in wearing position on the wearer, the side panels including a see-through portion and a second color; and
   (c) the landing zone including at least a first color, the first color of the landing zone is visible through at least the see-through portion of the side panels when the side panels are positioned over the landing zone, wherein the second color of the see-through portion of the side panel and the first color of the landing zone combine visually to produce a third color which is visible when the side panel is positioned over the landing zone.

2. The disposable absorbent article of claim 1 wherein at least one of the side panels includes a fastening tab comprising at least a part of the see-through portion.

3. The disposable absorbent article of claim 7 further including a colored disposal landing zone disposed on the garment-facing surface of the chassis, wherein the second color of the see-through portion of the side panel and the colored disposal landing zone combine visually to produce a fourth color which is visible when the see-through portion of the side panel is positioned such that the article is in a configuration for disposal.

* * * * *

UNITED STATES PATENT AND TRADEMARK OFFICE
CERTIFICATE OF CORRECTION

PATENT NO. : 6,733,483 B2
DATED : May 11, 2004
INVENTOR(S) : Michael Charles Raufman et al.

It is certified that error appears in the above-identified patent and that said Letters Patent is hereby corrected as shown below:

Drawings,
Replace Drawing Sheet 2 with the attached drawing sheet.

Column 4,
Line 24, delete "vairous" and insert -- various --.

Column 10,
Line 6, delete "5,928,212 ," and insert -- 5,928,212, --.
Line 45, delete "Mar. 20, 1990 ," and insert -- Mar. 20, 1990, --.

Column 13,
Line 3, delete "is relative" and insert -- relative --.

Column 16,
Line 26, delete "tongitudinal" and insert -- longitudinal --.
Line 27, delete "garment-feting" and insert -- garment-facing --.
Line 28, delete "front" and insert -- from --.
Line 53, delete "claim 7" and insert -- claim 1 --.

Signed and Sealed this

Fourth Day of April, 2006

JON W. DUDAS
*Director of the United States Patent and Trademark Office*